(12) United States Patent
Zeng et al.

(10) Patent No.: US 9,671,331 B2
(45) Date of Patent: Jun. 6, 2017

(54) APPARATUS FOR IMAGING HYDROGEN SULFIDE PLUME AND METHOD OF THE SAME

(71) Applicant: Providence Photonics, LLC, Baton Rouge, LA (US)

(72) Inventors: Yousheng Zeng, Baton Rouge, LA (US); Jonathan Morris, Baton Rouge, LA (US)

(73) Assignee: PROVIDENCE PHOTONICS, LLC, Baton Rouge, LA (US)

( * ) Notice: Subject to any disclaimer, the term of this patent is extended or adjusted under 35 U.S.C. 154(b) by 0 days.

(21) Appl. No.: 14/877,828

(22) Filed: Oct. 7, 2015

(65) Prior Publication Data

US 2016/0097714 A1 Apr. 7, 2016

Related U.S. Application Data

(60) Provisional application No. 62/061,032, filed on Oct. 7, 2014.

(51) Int. Cl.
*G01N 21/3504* (2014.01)
(52) U.S. Cl.
CPC ................ *G01N 21/3504* (2013.01)
(58) Field of Classification Search
CPC .................................................. G01N 21/3504
See application file for complete search history.

(56) References Cited

U.S. PATENT DOCUMENTS

| | | | | |
|---|---|---|---|---|
| 5,473,162 A | * | 12/1995 | Busch et al. | 250/341.6 |
| 2005/0264813 A1 | * | 12/2005 | Giakos | B82Y 20/00 |
| | | | | 356/369 |
| 2009/0321645 A1 | * | 12/2009 | Hinnrichs | 250/338.5 |
| 2010/0127173 A1 | * | 5/2010 | Schmidt | 250/338.5 |
| 2012/0153156 A1 | * | 6/2012 | Patel et al. | 250/338.5 |
| 2012/0241614 A1 | * | 9/2012 | Jonas et al. | 250/332 |
| 2015/0136982 A1 | * | 5/2015 | Kester | G01J 3/2823 |
| | | | | 250/332 |

* cited by examiner

*Primary Examiner* — David Porta
*Assistant Examiner* — Hugh H Maupin
(74) *Attorney, Agent, or Firm* — Robert E. Bushnell, Esq.

(57) ABSTRACT

As hydrogen sulfide is toxic and widely present in many oil and gas facilities, it is highly desirable to use an infrared camera to detect the presence of a hydrogen sulfide ($H_2S$) plume from a safe distance. The proposed are an imaging system and method for detecting hydrogen sulfide ($H_2S$) in a safe distance. The imaging system includes an infrared (IR) imager capable of capturing an image of a scene that includes a gas plume, and a narrow bandpass filter installed in the infrared imager. The narrow bandpass filter has a spectral window. A width of the spectral window is in the range of 100 nm to 300 nm. The spectral window is included in a wavelength range between 2.5 μm and 2.8 μm, a wavelength range between 1.5 μm and 2.0 μm, or a wavelength range between 7.0 μm and 10.0 μm.

19 Claims, 19 Drawing Sheets

FIG. 9

Table 1. Sensitivity analysis of candidate spectral regions for $H_2S$ imager

|  | Propane (for reference) | $H_2S$ (MWIR) | $H_2S$ (SWIR) | $H_2S$ (LWIR) | $H_2S$ (SWIR) |
|---|---|---|---|---|---|
| Bandpass filter spectral window | 3.2-3.4 μm | 3.65-3.75 μm | 2.55-2.70 μm | 8.0-8.1 μm | 1.9-2.0 μm |
| Min. ΔT (C) at CL=100,000 ppm-m | 1 | 100 | 8 | 35 | 100 |
| Min. CL (ppm-m) when ΔT=10 C | 700 | 500,000 | 85,000 | 300,000 | 480,000 |
| EPD (inches) | 0.03 | 19.69 | 3.35 | 11.81 | 18.9 |
| Contrast at CL=100,000 ppm-m & ΔT=10 C | 26.17% | 0.66% | 3.53% | 1.15% | 0.67% |

$FeS + 2HCl = FeCl_2 + H_2S$ $H_2S + CuSO_4 = CuS\downarrow + H_2SO_4$

APPARATUS FOR IMAGING HYDROGEN SULFIDE PLUME AND METHOD OF THE SAME

CLAIM OF PRIORITY

This application claims priority under 35 U.S.C. §119 to Provisional Patent Application No. 62/061,032, entitled "METHOD TO IMAGE HYDROGEN SULFIDE VAPOR PLUME" filed on Oct. 7, 2014, which application is incorporated herein by reference.

BACKGROUND OF THE INVENTION

Field of the Invention

This invention relates to an apparatus for an infrared (IR) imaging of hydrogen sulfide ($H_2S$) plumes from a distance, and a method of the same, in order to image and detect the hydrogen sulfide vapor in a safe distance.

Description of the Related Art

Hydrogen sulfide ($H_2S$) is a very toxic chemical. It is commonly found in oil and gas streams and some process streams at various concentrations. It is highly desirable to remotely image and detect the presence of $H_2S$ plumes from a distance in a similar fashion as imaging hydrocarbon vapor plumes using a special infrared (IR) camera. Unfortunately, due to its IR spectral characteristics, there has been no demonstrated apparatus and method to achieve IR imaging of $H_2S$ plumes.

SUMMARY OF THE INVENTION

It is an object of the present invention to provide an imaging system for detecting hydrogen sulfide in a safe distance.

In one embodiment, the imaging system includes an infrared (IR) imager capable of capturing an image of a scene that may include a gas plume, and a bandpass filter installed in the infrared imager. The infrared imager includes a sensor to generate an image of the scene. The image of the scene passes through the bandpass filter. The bandpass filter has a spectral window. A width of the spectral window is in a range of 100 nm to 300 nm. The spectral window is placed in a wavelength range between 2.5 µm and 2.8 µm, a wavelength range between 1.5 µm and 2.0 µm, or a wavelength range between 7.0 µm and 10.0 µm.

The imaging system may further include an illuminator to illumine the scene with an infrared light and enhance the $H_2S$ detection sensitivity. A wavelength of the infrared light of the illuminator is in the wavelength range of the spectral window of the bandpass filter.

The sensor of the infrared imager may be a long-wave infrared (LWIR) sensor if the bandpass filter has the spectral window of the wavelength range included between 8.0 µm and 8.1 µm or a substantially same spectral window. The sensor of the infrared imager may be a short-wave infrared (SWIR) sensor if the bandpass filter has the spectral window of the wavelength range included between 2.55 µm and 2.70 µm or a substantially same spectral window. The sensor of the infrared imager may be another SWIR sensor if the bandpass filter has the spectral window of the wavelength range included between 1.9 µm and 2.0 µm or a substantially same spectral window.

In another embodiment, a method for detecting hydrogen sulfide contained in a gas plume is provided. The method for detecting hydrogen sulfide includes steps of capturing an image of a scene that includes the gas plume by an infrared imager, obtaining an intensity of a background, which does not include the gas plume, from the image of the scene, obtaining an intensity of the gas plume from the image of the scene, calculating intensity difference between the intensities of the background and the gas plume, calculating a relative contrast that is the intensity difference divided by the intensity of the background, and determining whether the relative contrast is higher than a predetermined value. The infrared imager includes a sensor to detect the image. A bandpass filter is installed in the infrared imager. The image of the scene passes through the bandpass filter. The bandpass filter has a spectral window selected from the group consisting of a wavelength range included between 8.0 µm and 8.1 µm or a substantially same narrow spectral window to cover the $H_2S$ absorption band in this spectral region, a wavelength range included between 2.55 µm and 2.70 µm or a substantially same narrow spectral window to cover the $H_2S$ absorption band in this spectral region, and a wavelength range included between 1.9 µm and 2.0 µm or a substantially same narrow spectral window to cover the $H_2S$ absorption band in this spectral region.

The method further includes illumining the scene with an infrared light by an illuminator. A wavelength of the infrared light of the illuminator is in the wavelength range of the spectral window of the bandpass filter.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components.

FIG. 9 shows sensitivities in various spectral windows for imaging hydrogen sulfide.

DETAILED DESCRIPTION OF THE INVENTION

The present invention will now be described with reference to the accompanying drawings, in which an exemplary embodiment of the invention is shown.

Figure 1:
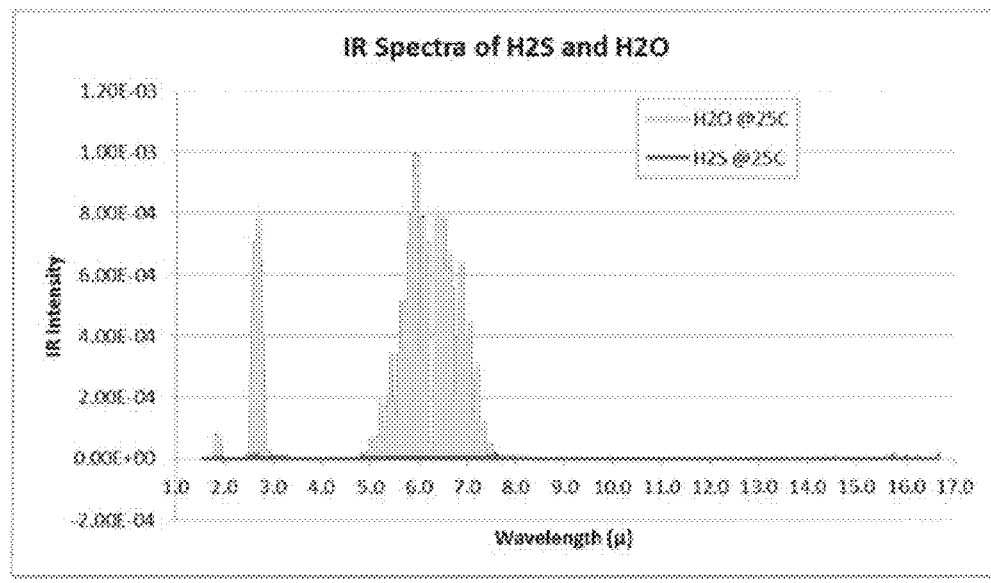
FIG. 1 shows infrared (IR) spectra of hydrogen sulfide ($H_2S$) and water vapor ($H_2O$).

FIG. 1 contains infrared (IR) spectra of hydrogen sulfide ($H_2S$) and water vapor ($H_2O$). The spectral data is can be obtained from a source such as the Pacific Northwest National Laboratory Vapor Phase Infrared Spectral Library (https://secure2. pnl.gov/nsd/nsd.nsf/Welcome). As can be seen in FIG. 1, the spectrum of $H_2S$ is overwhelmed by the spectrum of $H_2O$.

Figure 2:
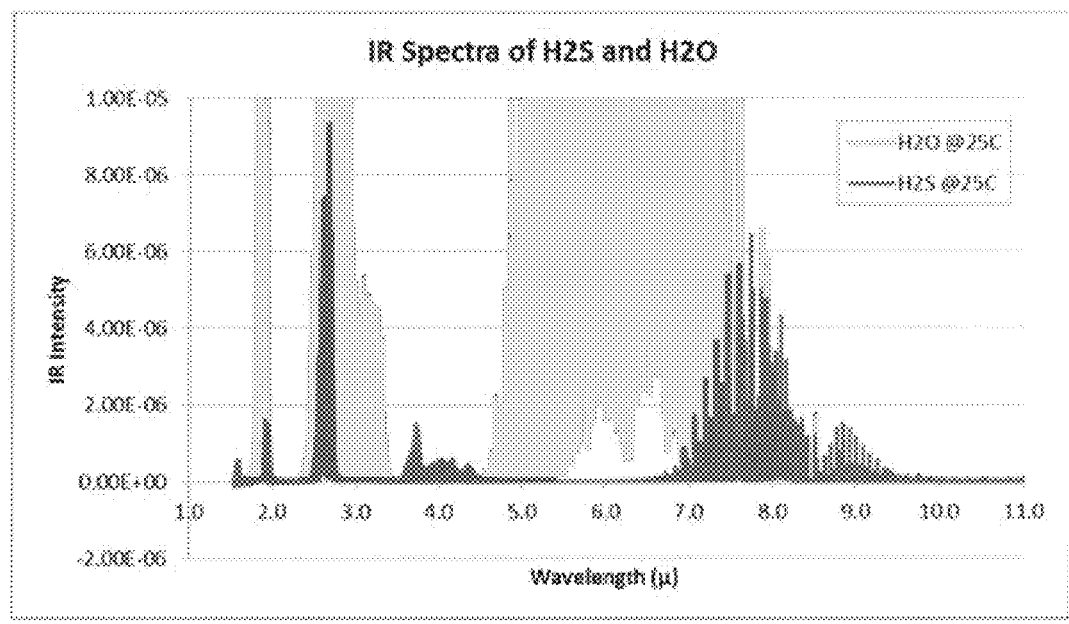
FIG. 2 shows zoomed in IR spectra of $H_2S$ and $H_2O$.

FIG. 2 contains the same IR spectra of $H_2S$ and $H_2O$, but with different scale to show details of $H_2S$ in the presence of $H_2O$. Based on the $H_2S$ spectrum shown in FIG. 2, there are four spectral regions that may be explored for IR gas imaging: a first short-wave IR (SWIR) region around 1.5-2 μm, a second SWIR region around 2.5-2.8 μm, a mid-wave IR (MWIR) region around 3.5-4.5 μm, and a long-wave IR (LWIR) region around 7-10 μm. The four candidate spectral regions are discussed below for their feasibility to be used for imaging $H_2S$ vapor.

Methodology used to evaluate technical feasibility.

The following simplified radiative transport equation (RTE) can be used to estimate the IR radiance received by an IR imager (or referred to as IR camera; the two terms are used interchangeably).

$$I = [\epsilon(\lambda)B(T_b, \lambda) - B(T_g, \lambda)]\exp^{[-\alpha(\lambda)CL]} + B(T_g, \lambda)$$

Where:
I=IR intensity received by the IR camera.
λ=wavelength, in micrometer or μ.
$\epsilon(\lambda)$=emissivity of background scene at wavelength λ.
$T_b$=background temperature, in deg. K.
$T_g$=temperature of gas/vapor, in deg. K.
B(T,λ)=blackbody radiation per Plank's Law at temperature T (background or gas) and wavelength λ.
$\alpha(\lambda)$=absorption coefficient of gas in question at wavelength λ, i.e., specific value in the IR spectrum at wavelength λ. Unit: $ppm^{-1} m^{-1}$.
C=concentration of gas in question, in parts per million (ppm).
L=optical path length of gas plume, in meter (m).

The above equation is used to calculate IR intensity received by a pixel of the IR camera that represents an area in the image that has target gas or vapor. This gas intensity is denoted as $I_G$. The same intensity calculation can be done for a nearby pixel of the IR camera where there is no target gas or vapor, i.e., the intensity of the background scene. This background intensity is denoted as $I_B$. The background intensity can also obtained from the same pixel in a neighboring frame when the gas plume has shifted away and the background scene is not obscured by the gas. The gas plume can be imaged and recognized when there is sufficient intensity difference $\Delta I$ ($=I_B-I_G$) between the two intensities, i.e., $\Delta I=I_B-I_G$ is significant with respect to the absolute value of the background intensity $I_B$. The intensity difference $\Delta I$ represents the contrast between the gas plume and the background in the scene. Due to order of magnitude differences in IR radiance in most scenes, it is better to use relative contrast expressed as percentage of background intensity, i.e., $\Delta I/I_B$ (%). A gas plume generally becomes recognizable in an image when the relative contrast ($\Delta I/I_B$) is in the neighborhood of 3% or higher for each gas plume pixel and there are sufficient number of pixels in a cluster representing the gas plume.

Imaging propane as a benchmark.

Figure 3:
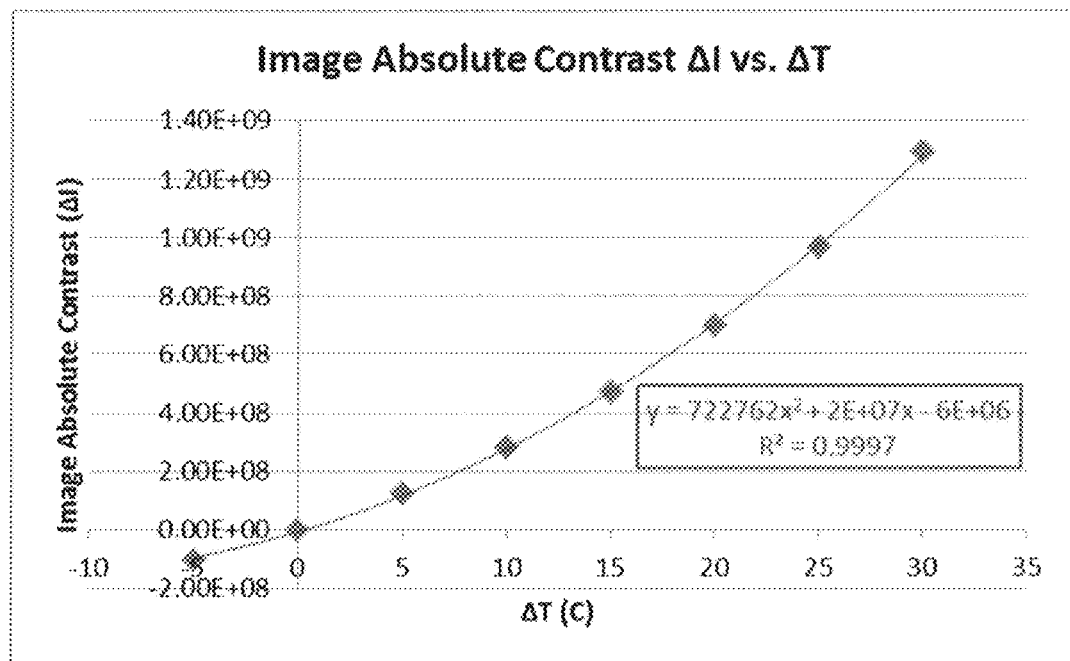
FIG. 3 shows an absolute contrast for propane (bandpass filter 3.2-3.4 µm, CL=100,000 ppm-m).
Figure 4:
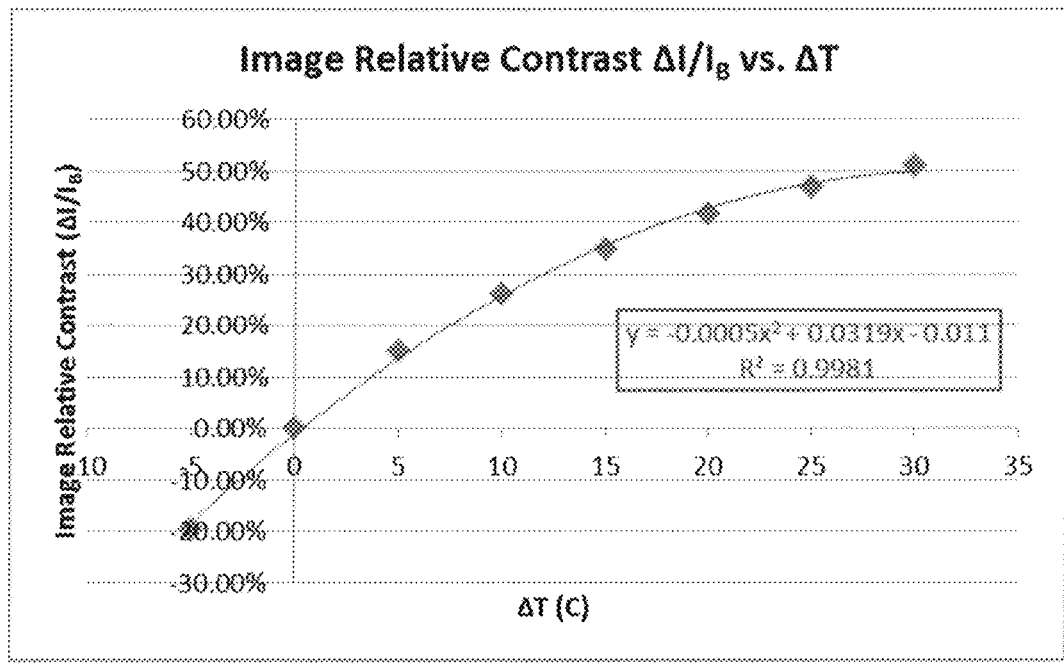
FIG. 4 shows a relative contrast for propane (bandpass filter 3.2-3.4 µm, CL=100,000 ppm-m).

Using a gas imaging IR camera to image propane is well established. Therefore, propane is used as a benchmark for this feasibility evaluation and preliminary design. FIG. 3 is a intensity difference $\Delta I$ versus temperature difference $\Delta T$ ($=T_B-T_G$, difference between the background temperature and the gas temperature) plot generated using the methodology described in the above section and a theoretical cold filter with a bell-shaped transmittance curve centered on the absorption band of propane in the mid-wave IR (about 3.2-3.4 μm). The plot was generated assuming CL=100,000 ppm-m (parts-per-million meter), equivalent to a one meter deep plume at a concentration of 10%. While FIG. 3 represents the theoretical absolute contrast (AC), $\Delta I$, for a propane plume, FIG. 4 represents the theoretical relative contrast (RC), $\Delta I/I_B$, for propane under the same conditions. As the temperature difference $\Delta T$ departs from zero, the relative contrast increases (or decreases) and the plume becomes visible due to increased contrast between the plume and the background. As stated earlier, when the relative contrast reaches approximately 3%, the plume should be readily recognizable in the image. As the relative contrast further increases, the plume becomes darker and darker. The relative contrast can be high due to either a high temperature difference $\Delta T$ or a high product of concentration (C) and optical path length (L), i.e., CL. Consequently, one can hold either $\Delta T$ or CL constant and reduce the other until relative contrast is reduced to 3% (assuming RC=3% is the threshold for plume recognition). In this way, detectability of chemical vapor can be characterized in terms of a minimum $\Delta T$ under a given CL or a minimum CL under a given $\Delta T$.

For propane, at a constant CL=100,000 ppm-m, the minimum temperature difference $\Delta T$ to generate a recognizable plume (RC>threshold of 3%) is approximately 1° C. At a constant $\Delta T=10°$ C., the minimum CL to generate a recognizable plume (RC>threshold of 3%) is approximately 700 ppm-m. The equivalent plume depth (EPD) of pure gas (100% or 1,000,000 ppm) for this 700 ppm-m value is 0.0007 m (or about 0.03 inches). The EPD can also be loosely viewed as equivalent plume diameter. It should be noted that when EPD is very small (highly detectable compounds), the plume recognition may become limited by the spatial (pixel) resolution of the camera rather than limited by contrast.

Hydrogen sulfide ($H_2S$) in the mid-wave infrared (MWIR) of 3.5-4.5 μm.

Figure 5:
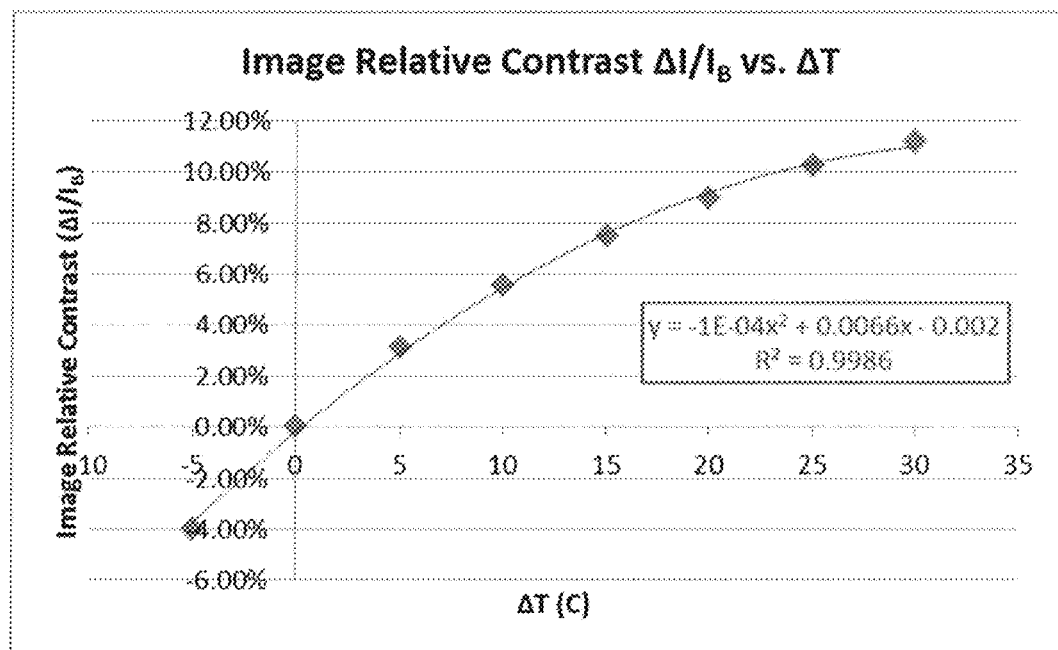
FIG. 5 shows a relative contrast for $H_2S$ (rectangular bandpass filter 3.65-3.75 µm, CL=1,000,000 ppm-m).

This spectral region was first selected because there is minimum interference from water ($H_2O$) spectrum (as shown in FIG. 2). However, the $H_2S$ absorption coefficient is very low in this region. Several bandpass filter transmittance windows have been simulated and the best one is a window of 3.65-3.75 μm. FIG. 5 is the relative contrast (RC) vs. temperature difference $\Delta T$ plot at CL=1,000,000 ppm-m. Notice that the CL is set at 10 times higher than similar plot for propane (FIG. 4), yet the RC is still nearly an order of magnitude lower than that of propane. If the CL is set at 100,000 ppm-m, the term of -αCL in the radiative transport equation (RTE) above is so small and the term of exp(-αCL) is so close to 1, no matter how high the ΔT is, it will not create a RC greater than 3%. Therefore it is technically infeasible to image $H_2S$ in this spectral region at CL in the neighborhood of 100,000 ppm-m. At ΔT=10 C, CL=500,000 ppm-m may generate enough contrast to create a plume image. That means a nearly 20-inch diameter plume of 100% $H_2S$ (or a 17-foot diameter vapor cloud containing 10% $H_2S$) may have a chance to form a vapor image. This sensitivity is too low for most applications.

Hydrogen sulfide ($H_2S$) in the long-wave IR (LWIR) of 7.0-10.0 μm.

Figure 6:
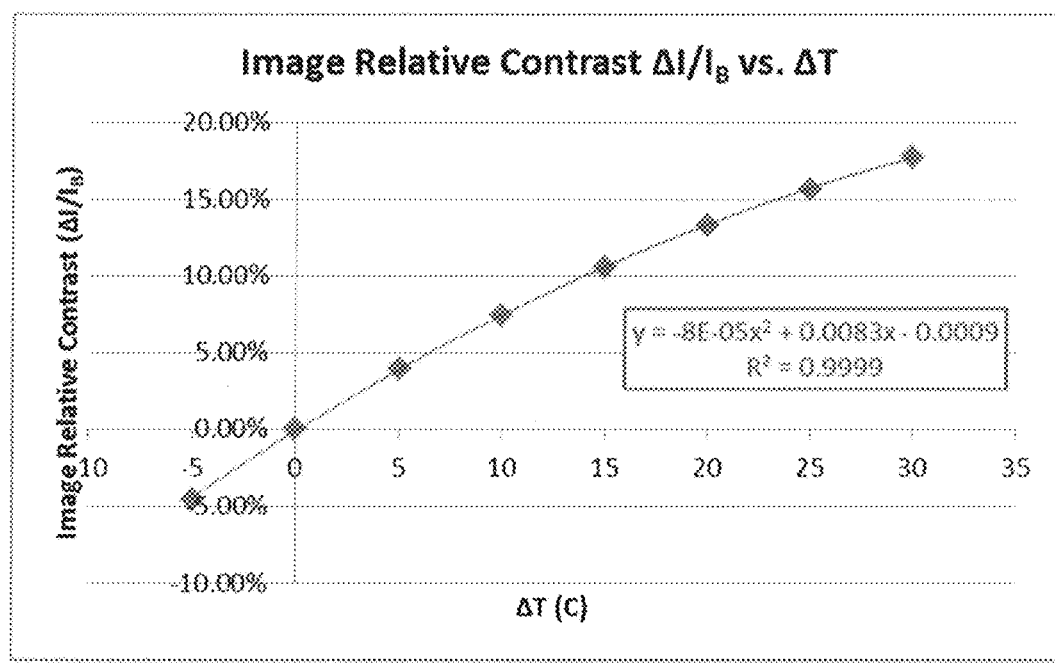
FIG. 6 shows a relative contrast for $H_2S$ (rectangular bandpass filter 8.0-8.1 µm, CL=1,000,000 ppm-m).

Having concluded that the $H_2S$ spectral region in 3.5-4.5 μm is too insensitive and not suitable for gas imaging, the next candidate spectral region is in the Long-Wave IR (LWIR) of 7-10 μm (as shown in FIG. 2). After multiple simulations, the bandpass filter is selected at 8.0-8.1μm. FIG. 6 is a relative contrast (RC) vs. temperature difference ΔT plot similar to FIG. 5. The CL is still set at high value of 1,000,000 ppm-m instead of 100,000 ppm-m. Comparing FIG. 5 and FIG. 6, it can be seen that for the same ΔT, the RC is higher in FIG. 6 than FIG. 5. The LWIR region is an improvement, but the sensitivity is still low. If the CL is set at 100,000 ppm-m, a RC of 3% can be achieved at ΔT of 35 C, which is a ΔT that is not likely to be encountered in practice. At ΔT=10° C., CL=300,000 ppm-m may generate enough contrast to create a $H_2S$ plume image. That means a nearly 12-inch diameter plume of 100% $H_2S$ (or a 10-foot diameter vapor cloud containing 10% $H_2S$) may have a chance to form a vapor image. This sensitivity is still low.

Although there is some overlap between the $H_2S$ spectrum and $H_2O$ spectrum in the 8.0-8.1 μm window, the effect of ambient $H_2O$ is small, less than 1% assuming the atmosphere contains 2% of $H_2O$ and the distance from the $H_2S$ plume to the camera is 10 meters.

Hydrogen sulfide ($H_2S$) in the second short-wave IR (SWIR) of 2.5-2.8 μm.

Figure 7:
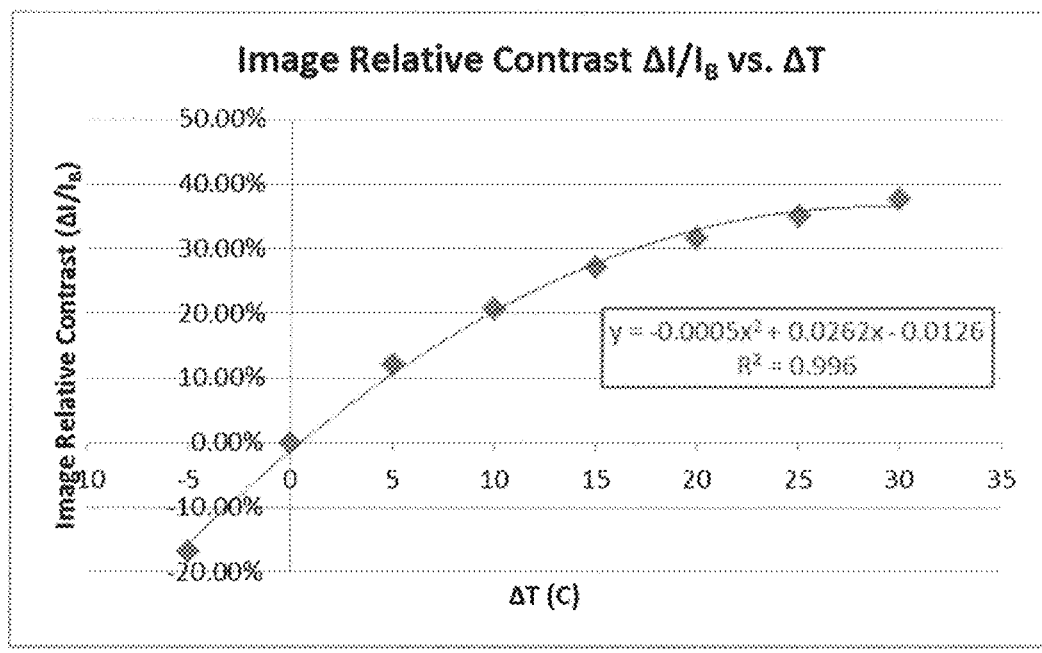
FIG. 7 shows a relative contrast for $H_2S$ (rectangular bandpass filter 2.55-2.7 µm, CL=1,000,000 ppm-m).

The third spectral region evaluated is in the second SWIR 2.5-2.8 μm. The $H_2S$ band in this region overlaps with a band of $H_2O$ spectrum (as shown in FIG. 2). However, the sensitivity in terms of RC is better (see FIG. 7, and comparing to FIG. 5 and FIG. 6). FIG. 7 is also based on CL=1,000,000 ppm-m so it can be compared to FIG. 5 and FIG. 6. However, due to the higher sensitivity, imaging $H_2S$ plume at CL=100,000 ppm-m seems much more feasible. The minimum ΔT for generating a RC>3% is 8° C., a very practical ΔT. This sensitivity measure is achieved with a bandpass filter window of 2.55-2.70 μm. At ΔT=10° C., the minimum CL is 85,000 ppm-m. That means approximately a 3.4-inch diameter plume of 100% $H_2S$ (or a 2.8-foot diameter vapor plume containing 10% $H_2S$) may have a chance to form a vapor image and be detected.

As indicated in FIG. 2, this spectral region (2.5-2.8 μm) overlaps with a significant spectral band of water vapor. The effect of water content in the ambient air is expected to attenuate the $H_2S$ IR signal. This effect is further evaluated in a later section. This spectral region is in the short-wave IR (SWIR). The reflected light (e.g., from daylight in day time or starlight at night) plays a larger role in the SWIR region. It may add more background IR energy to what is predicted by Plank's law, and potentially enhance gas imaging.

Hydrogen sulfide ($H_2S$) in the first short-wave IR (SWIR) of 1.5-2.0 μm.

Considering the enhanced effect due to reflected light in SWIR, one more spectral region is evaluated for this analysis, which are the two small $H_2S$ peaks in the 1.5-2.0 μm region (as shown in FIG. 2). The result purely based on the thermal IR radiance (not including the reflected light) is not very promising. When CL=100,000 ppm-m, ΔT needs to be over 100 C to generate a contrast greater than 3%. At ΔT=10 C, the minimum CL will be 480,000 ppm-m, or EPD of 18.9 inches. The result is comparable to the spectral region in 3.5-4.5 μm. The only way this SWIR region will work better is to rely primarily on the reflected light.

The results of the above analyses for four candidate spectral regions are summarized in Table 1 shown in FIG. 9. Based on the information presented in Table 1, the most promising spectral region for $H_2S$ is the second SWIR with a bandpass filter window of 2.55-2.70 μm. It will not be as sensitive as propane. However, it should be technically feasible.

Effect of water content in atmosphere.

Figure 8:
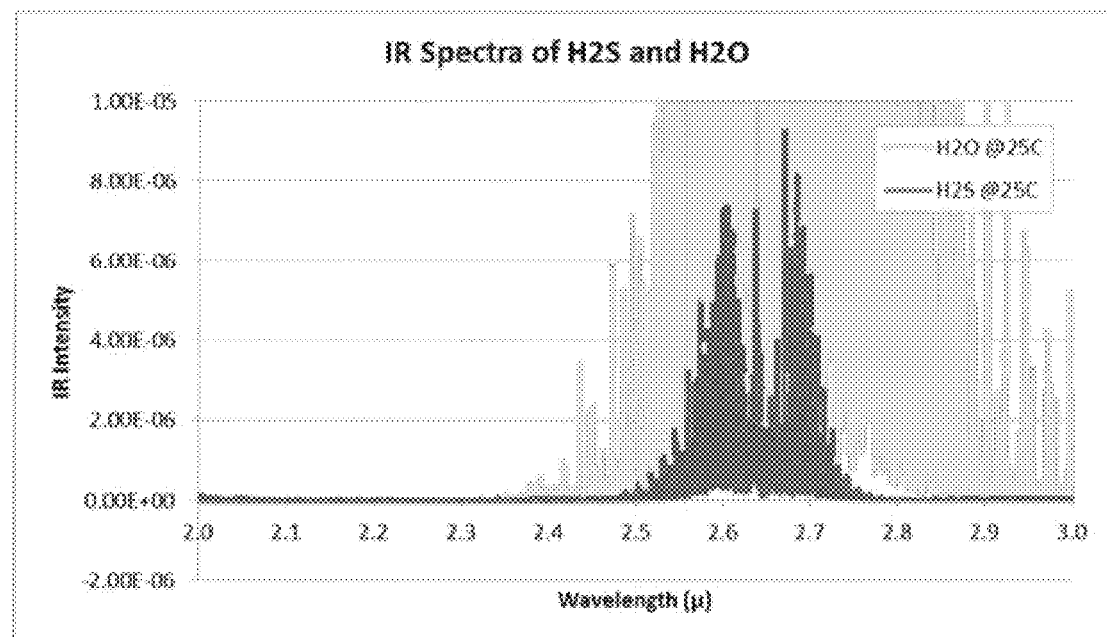
FIG. 8 shows enlarged spectra of $H_2S$ and $H_2O$ in 2.0-3.0 µm.
Figure 10:
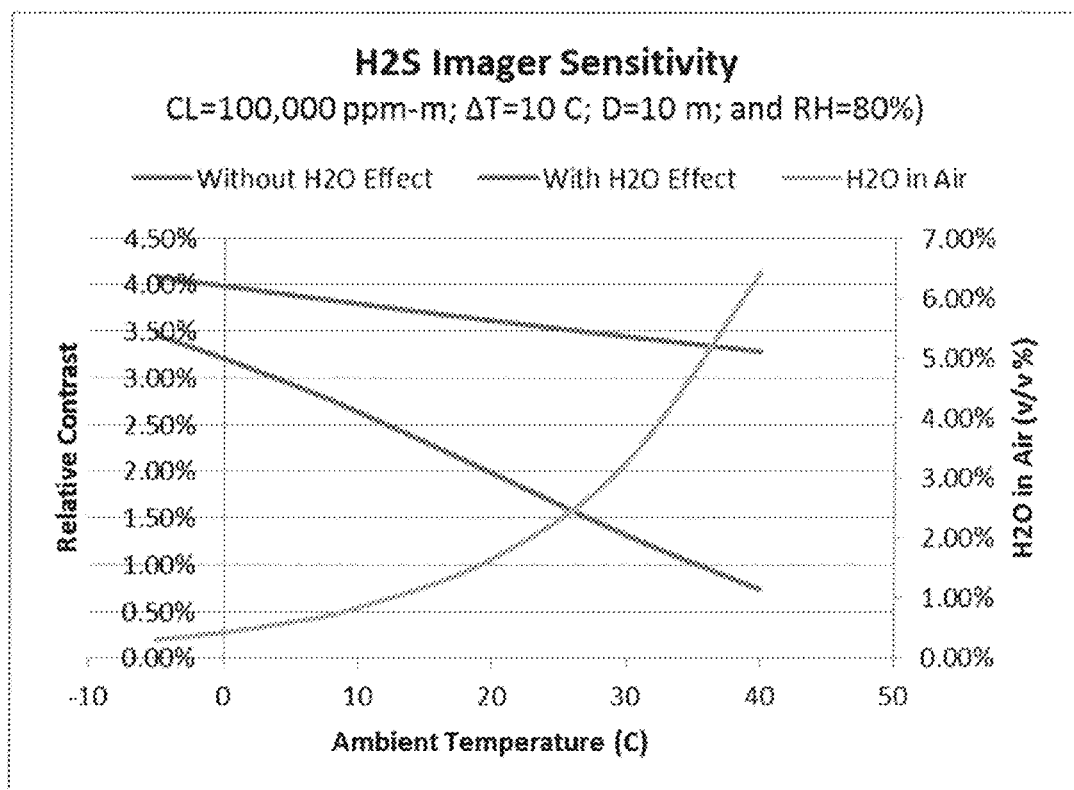
FIG. 10 shows an effect of atmospheric water vapor on $H_2S$ sensitivity at various ambient temperatures.

Although the second SWIR window of 2.55-2.70 (or a substantially same narrow spectral window to cover the $H_2S$ absorption band in this spectral region) has the highest sensitivity for imaging $H_2S$, there is significant overlap of water band in this spectral region (see FIG. 2, also see enlarged plot in FIG. 8). Therefore, the effect of water vapor in the atmosphere cannot be ignored. The effect of water vapor in the atmosphere is illustrated in FIG. 10 through FIG. 13. In these four figures, the effect of one variable is examined while holding all other variables constant. In FIG. 10, as ambient temperature increases, the water content increases given a constant relative humidity (RH) of 80% (the green line in FIG. 10). More water in the air causes more attenuation of the $H_2S$ IR radiance. As a result, the relative contrast of $H_2S$ plume decreases.

Figure 11:
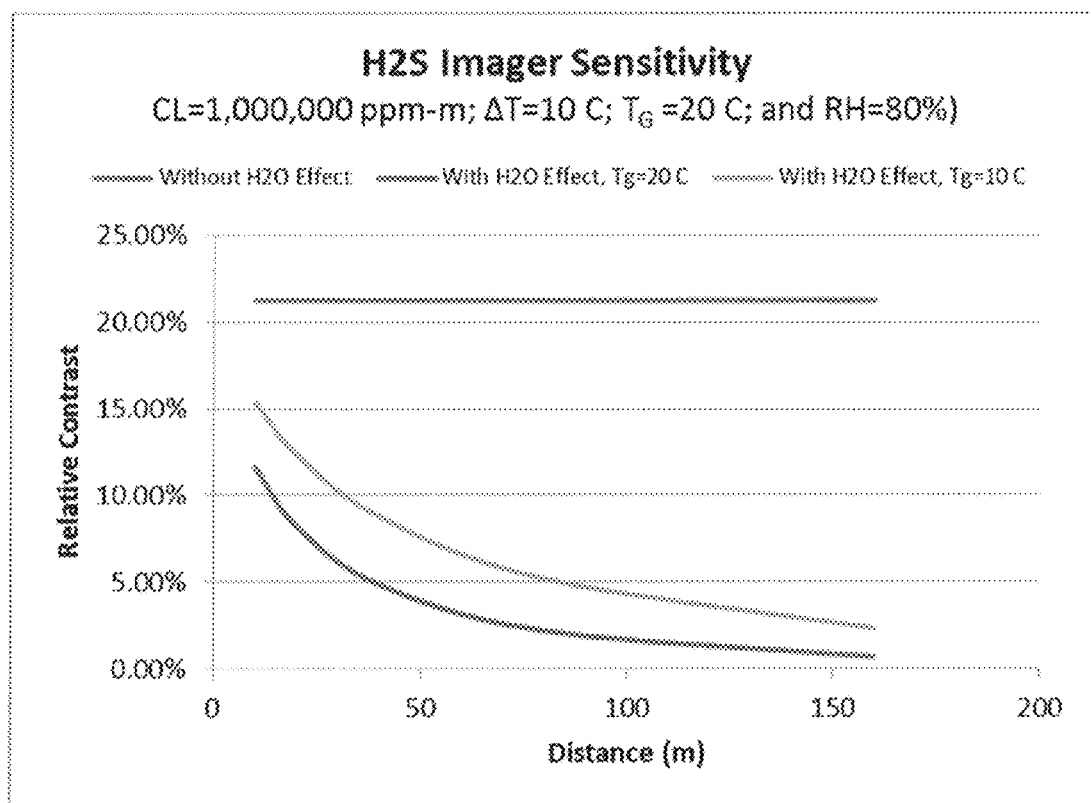
FIG. 11 shows an effect of atmospheric water vapor on $H_2S$ sensitivity at various distances.

In FIG. 11, the distance from the $H_2S$ plume to the imager increases while holding all other variables constant. As the distance increases, the length of the path that $H_2S$ IR rays travel to the imager increases, and more IR rays are absorbed by the water vapor in the atmosphere reducing the relative contrast of the $H_2S$ plume. FIG. 11 shows this effect at two ambient temperatures (or gas temperatures, $T_G$) of 10° C. and 20° C.

Figure 12:
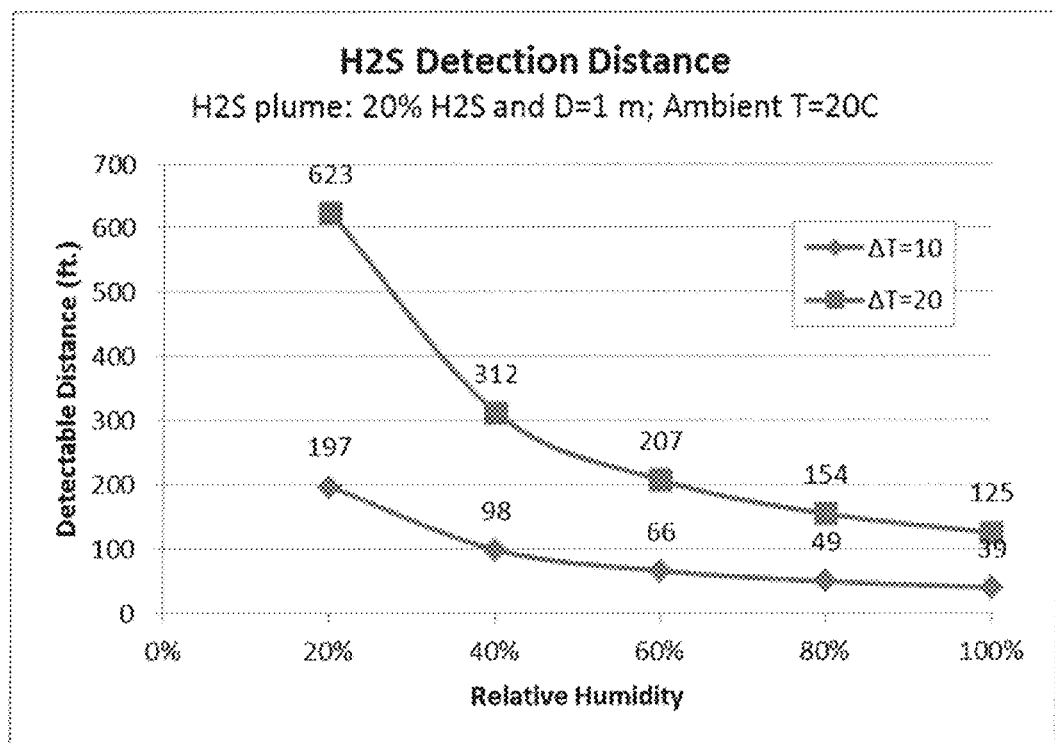
FIG. 12 shows a detectable distance for a $H_2S$ plume that contains 20% $H_2S$ and a diameter of 1 m (3.28 ft).

FIG. 12 shows the expected detectable distance of a $H_2S$ plume that contains 20% $H_2S$ and has a diameter of 1 m (3.28 ft.), i.e., CL=200,000 ppm-m. FIG. 12 is generated based on the assumption that the $H_2S$ plume is detectable when the relative contrast is 3% or higher (i.e., RC~3%). Ambient temperature of 20° C. is also assumed. Two different temperature difference ΔT values are illustrated in FIG. 12. When ΔT is 10° C., the detectable distance ranges from 39 ft to 197 ft. depending on RH. When ΔT is 20° C., the detectable distance improves to a range of 125 to 623 ft. depending on RH. It should be noted that these ΔT values are based on apparent temperature (as opposed to actual temperature measured by a conventional thermometer) and is realistic for real world applications. The apparent temperature is the temperature calculated based on blackbody calibration and the total IR radiance received by the IR camera, including the IR energy emitted by the background object (the emissive component), the IR energy reflected by the background (the reflective component), and IR energy transmitted through the background (the transmission component).

The above discussion addresses the effect of water in the atmosphere between the $H_2S$ plume and the imager. The water in the atmosphere between the background and the $H_2S$ plume also has an impact on the $H_2S$ image. In order to generate any gas image, there must be a sufficient temperature difference ΔT between the background and the gas plume. When the spectral window used for this $H_2S$ imager has significant overlap with water absorption band, the water molecules between the background and the $H_2S$ plume attenuate the IR radiance in this spectral window, effectively reducing the effect of $\Delta T$ (reducing the IR illumination from the background) and decreasing the contrast between the plume and the background.

Figure 13:
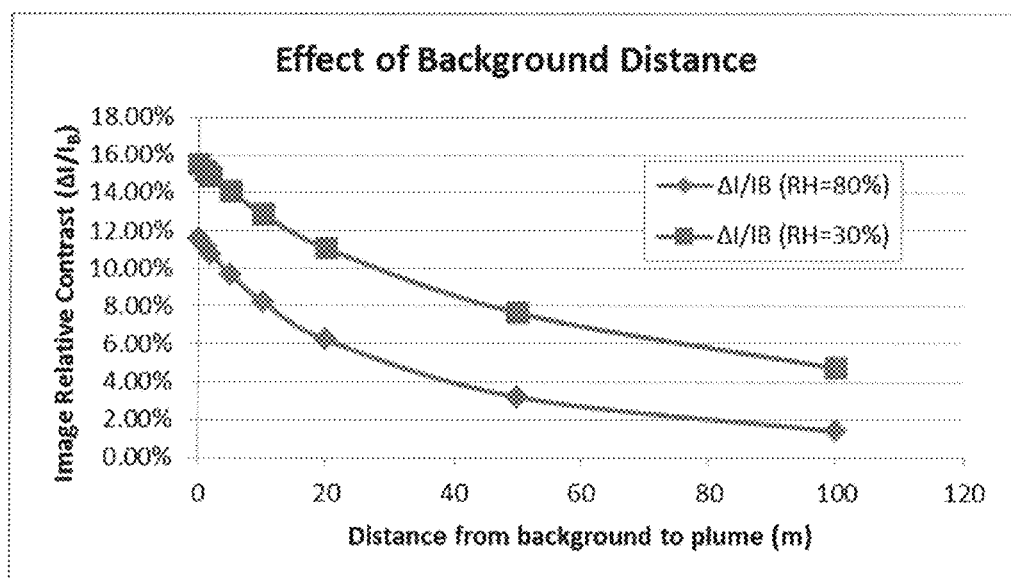
FIG. 13 shows an effect of background-to-plume distance. CL=1,000,000 ppm, Tb=30 C, Ta=20 C, T=10 C, RH=80%, distance from plume to camera=10 m.

The degree of impact due to the presence of water in the atmosphere between the background and the plume is a function of the water content in the air (i.e., RH and ambient temperature) and the distance from the background to the plume. When all other parameters are held constant, the effect of water in the atmosphere increases as the distance between the background and the plume increases, as illustrated in FIG. 13.

Specially designed IR imagers (IR cameras) equipped with a narrow bandpass filter have been used to image gaseous materials (e.g., hydrocarbon leaks). Such gas detection IR cameras are commercially available. However, there are no IR cameras that can detect hydrogen sulfide ($H_2S$) vapor. It is highly desirable to use an IR camera to detect the presence of a hydrogen sulfide ($H_2S$) plume from a safe distance as $H_2S$ is very toxic and widely present in many oil and gas facilities.

The analysis documented in this specification leads to the invention of a hydrogen sulfide ($H_2S$) detection IR imager. One embodiment of the invention is to construct an IR camera with a short-wave infrared (SWIR) sensor and a bandpass filter in the spectral window of 2.55-2.70 μm (or a substantially same narrow spectral window to cover the $H_2S$ absorption band in this spectral region). This design has the highest sensitivity for $H_2S$, despite the fact that it overlaps with a spectral band of water vapor in the atmosphere. Due to this water interference, it has been perceived that an IR imager in this spectral region is unworkable. As a result, no gas imaging IR cameras are designed and manufactured in this spectral region. The significance of this invention is that through the analysis documented in this specification, it has been demonstrated that such an IR camera design will provide the best performance for $H_2S$ detection. The detection capability has been characterized under a variety of environmental variables, including: apparent background temperature ($T_B$), $H_2S$ plume temperature ($T_G$), the difference between the above two temperatures ($\Delta T=T_B-T_G$), ambient temperature ($T_A$), relative humidity (RH), distance from the plume to the camera, and distance from the background to plume. Herein, the SWIR sensor is defined as a sensor that is capable of effectively detecting the intensity of light having the wavelength included in the range between 2.5 μm and 2.8 μm.

For a gaseous plume that contains 20% of $H_2S$ and has a diameter of 1 m (3.28 ft.), an IR camera designed based on this invention can detect such a $H_2S$ plume (or a larger plume/more concentrated plume) at various distances (up to 600 ft. or greater depending on aforementioned variables). These distances are practical for end users (e.g., personnel in oil and gas industry, emergency responders, etc.). The hydrogen sulfide ($H_2S$) IR camera can be equipped with firmware that can provide users with relevant information regarding the camera's sensitivity based on user entered data such as ambient temperature, relative humidity, and distance.

Another embodiment of this invention is to construct an IR camera with a long-wave infrared (LWIR) sensor and a bandpass filter in the spectral window of 8.0-8.1 μm (or a variation of this spectral window in the spectral region of 7.5-9.5 μm). This design will have less interference from water vapor in the atmosphere. However, the sensitivity is expected to be approximately one order of magnitude lower than the above IR camera with bandpass filter of 2.55-2.70 μm. Herein, the LWIR sensor is defined as a sensor that is capable of effectively detect the intensity of light having the wavelength included in the range between 7 μm and 10 μm. In the same way a short-wave infrared (SWIR) sensor is defined as a sensor that is capable of effectively detect the intensity of light having the wavelength included in the range between 1.5 μm and 3.0 μm.

As analyzed in this specification, there are two more spectral regions that could be utilized for $H_2S$ gas imaging. One of them is the mid-wave infrared (MWIR) near 3.65-3.75 μm and the other one is the short-wave infrared (SWIR) near 1.9-2.0 μm. If imagers were constructed based on these two designs, the sensitivity would be extremely low and could be able to detect a large hydrogen sulfide ($H_2S$) cloud.

For the two embodiments of this invention that use SWIR (1.90-2.0 μm and 2.55-2.70 μm), the characteristics of the surfaces in the background may enhance the $H_2S$ detection sensitivity. The surfaces that are more reflective (i.e., low emissivity) such as steel will increase the reflected IR energy and potentially increase the contrast for imaging $H_2S$.

In another embodiment of this invention, an active IR source is provided to illuminate the scene with infrared energy covering the same wavelength as the bandpass filter. This illuminator could be co-located with the camera or it could be placed in the field of view directed back to the camera. If this illuminator is co-located with the camera then a low emissivity surface (e.g., aluminum foil) may be placed in the field of view to reflect the infrared energy back to the imager. Alternatively, the surfaces in the field of view would be wrapped with aluminum foil or coated with a low emissivity paint (e.g., aluminum-containing paint) to reflect the infrared energy back to the imager.

Figure 14:
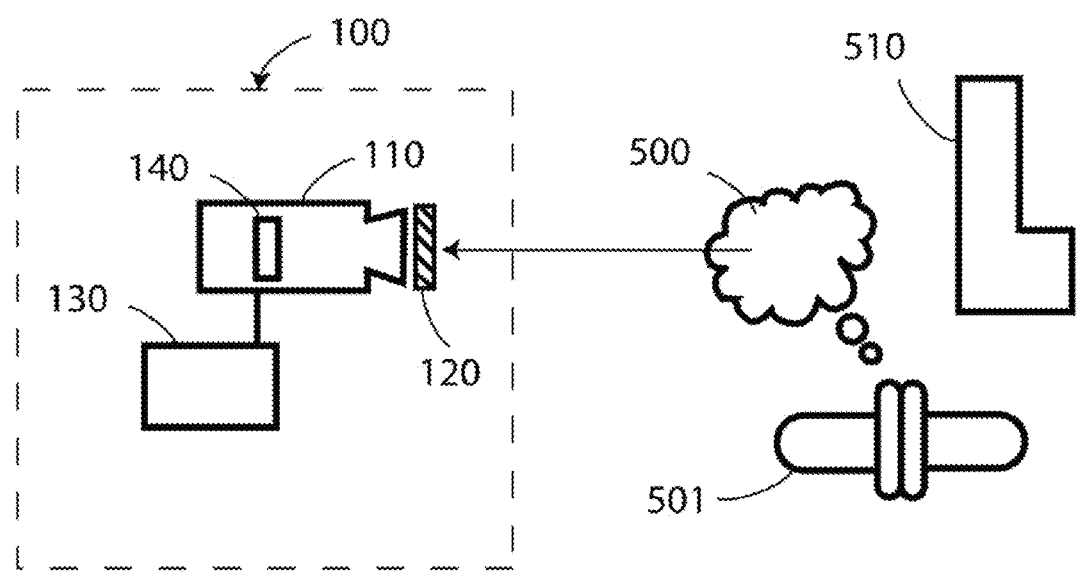
FIG. 14 shows an imaging system for imaging hydrogen sulfide (H2S) constructed as an embodiment of the present invention.

The embodiments of this invention can be achieved by constructing an imaging system including an infrared imager. Referring to FIG. 14, the imaging system 100 for imaging hydrogen sulfide ($H_2S$) includes an infrared (IR) imager 110 to capture images of a scene that includes a gas plume that may include hydrogen sulfide, and an analysis unit 130 that collects imaging data from the imager 110 and analyzes the imaging data. The imaging system 100 includes a bandpass filter 120 that can be installed inside the imager 110 or can be installed outside the imager 110. The bandpass filter 120 has a spectral window of wavelengths. Light having a wavelength in this spectral window of the bandpass filter can pass this bandpass filter while light having a wavelength outside this spectral window may be blocked in the bandpass filter 120. The IR imager 110 includes a sensor 140 that can detect an intensity of light having wavelength included in the spectral window of the bandpass filter 120. The gas plume 500, which may include hydrogen sulfide ($H_2S$), is produced from a piece of equipment 501, and is monitored by the imaging system 100. The reference numeral 510 indicates a background that represents all background objects in the scene, which may include equipment 501 that produces the gas plume 500.

As described above, the imaging system 100 can employ various types of bandpass filters. When the IR imager 110 is equipped with a short-wave infrared (SWIR) sensor, the bandpass filter 120 can be a bandpass filter having the spectral window included in the wavelength range of 2.55-2.70 μm (or a substantially same spectral window) or a bandpass filter having the spectral window included in the wavelength range of 1.9-2.0 μm (or a substantially same spectral window). When the IR imager 110 is equipped with a long-wave infrared (LWIR) sensor, the bandpass can be a bandpass filter having the spectral window included in the wavelength range of 8.0-8.1 µm (or a substantially same spectral window). However, these spectral windows of the bandpass filter are not limited as described in these examples. The spectral window of the bandpass filter may have a certain spectral size or width. The width of the spectral window of the bandpass filter may be in the range of 100 nanometer (nm) to 300 nm.

Figure 15:
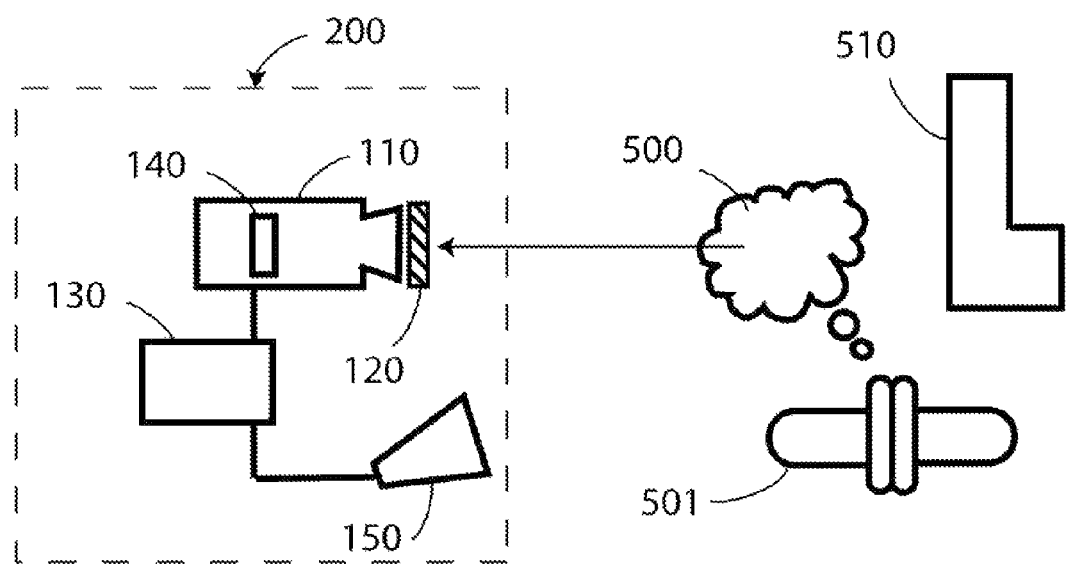
FIG. 15 shows an imaging system for imaging hydrogen sulfide (H2S) constructed as another embodiment of the present invention.

In another embodiment referring to FIG. 15, the imaging system 200 further includes an illuminator 150. The illuminator works as an active source to illuminate the scene with infrared light having a wavelength included in the spectral window of the bandpass filter 120 installed in the IR imager 110. Referring to FIG. 15, the imaging system 200 for imaging hydrogen sulfide ($H_2S$) includes an infrared (IR) imager 110 to capture images of hydrogen sulfide gas plume, and an analysis unit 130 that collects imaging data from the imager 110 and analyzes the imaging data. The illuminator 150 can be coupled to the analysis unit 130, and the operation of the illuminator can be controlled by the analysis unit 130. However, the illuminator 150 can be placed independently from the analysis unit 130. In this case, the operations of the illuminator 150 can be controlled by a user. This illuminator 150 could be co-located with the IR imager 110 or it could be placed in the field of view directed back to the IR imager 110. If this illuminator 150 is co-located with the IR imager 110, then a low emissivity surface may be placed in the field of view to reflect the infrared energy back to the IR imager 110.

The imaging system 200 of this embodiment includes an infrared (IR) imager 110 to capture images of a scene that includes a gas plume that may include hydrogen sulfide, and an analysis unit 130 that collects imaging data from the imager 110 and analyzes the imaging data. The imaging system 200 includes a bandpass filter 120 that can be installed inside the imager 110 or can be installed outside the imager 110. The bandpass filter 120 has a spectral window of wavelengths. Light having a wavelength in this spectral window of the bandpass filter can pass this bandpass filter while light having a wavelength outside this spectral window may be blocked in the bandpass filter 120. The IR imager 110 includes a sensor 140 that can detect an intensity of light having wavelength included in the spectral window of the bandpass filter 120. The gas plume 500, which may include hydrogen sulfide ($H_2S$), is produced from a piece of equipment 501, and is monitored by the imaging system 200. The reference numeral 510 indicates a background that represents all background objects in the scene, which may include equipment 501 that produces the gas plume 500.

As the same as the imaging system shown in FIG. 14, the imaging system 200 can employ various types of bandpass filters. When the IR imager 110 is equipped with a short-wave infrared (SWIR) sensor, the bandpass filter 120 can be a bandpass filter having the spectral window included in the wavelength range of 2.55-2.70 µm (or a substantially same spectral window) or the spectral window included in the wavelength range of 1.5-2.0 µm (or a substantially same spectral window). When the IR imager 110 is equipped with a long-wave infrared (LWIR) sensor, the bandpass can be a bandpass filter having the spectral window included in the wavelength range of 8.0-8.1 µm (or a substantially same spectral window). However, these spectral windows of the bandpass filter are not limited as described in these examples.

Figure 16:
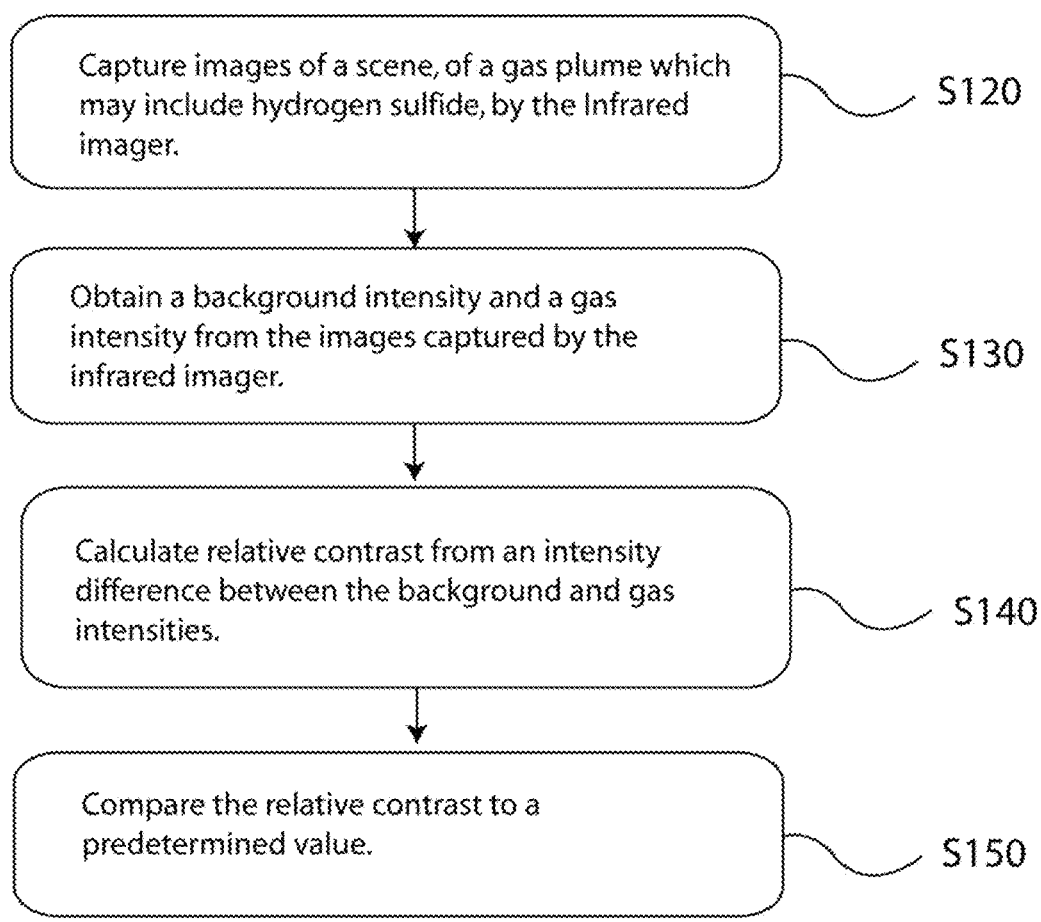
FIG. 16 shows a flowchart for the method for detecting hydrogen sulfide ($H_2S$) in gas plume constructed as an embodiment of the present invention.

In another embodiment, a method for detecting hydrogen sulfide ($H_2S$) in gas plume is proposed. FIG. 16 shows a flowchart that illustrates the processes of detecting hydrogen sulfide ($H_2S$) in gas plume. Referring to FIG. 16, an image of a scene of a gas plume, which may include hydrogen sulfide ($H_2S$), are captured by the IR imager 110 (S120) by an infrared (IR) imager that is installed with a bandpass filter having a certain spectral window and includes a sensor to detect light in the spectral window of the bandpass filter. The objects in the scene include the gas plume 500 and the background 510, which may include equipment 501, shown in FIGS. 14 and 15, from which the gas plume 500 may be produced. By analyzing pixels of the image captured by the IR imager 110, an intensity of background $I_B$ and an intensity of gas (hydrogen sulfide) $I_G$ are obtained (S130). By calculating the intensity difference $\Delta I$ ($=I_B-I_G$) between the background and gas intensities, a relative contrast (RC=$\Delta I/I_B$) is calculated (S140). Then, this relative contrast is compared to a predetermined value (S150). If the relative contrast is higher than a predetermined value, it is determined that the gas plume monitored by the IR imager 110 includes hydrogen sulfide ($H_2S$).

Figure 17:
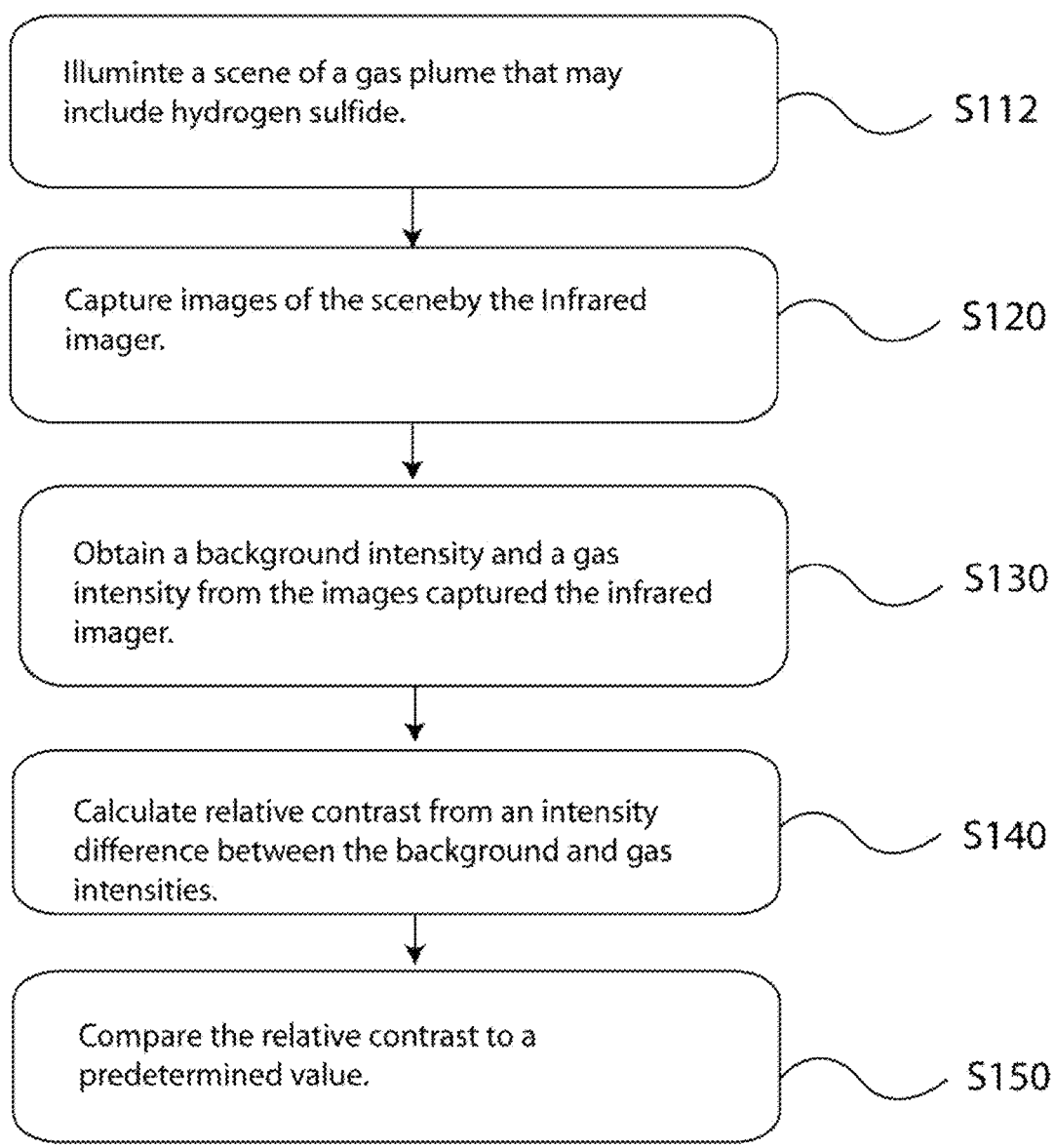
FIG. 17 shows a flowchart for the method for detecting hydrogen sulfide ($H_2S$) in gas plume constructed as another embodiment of the present invention.
Figure 18:
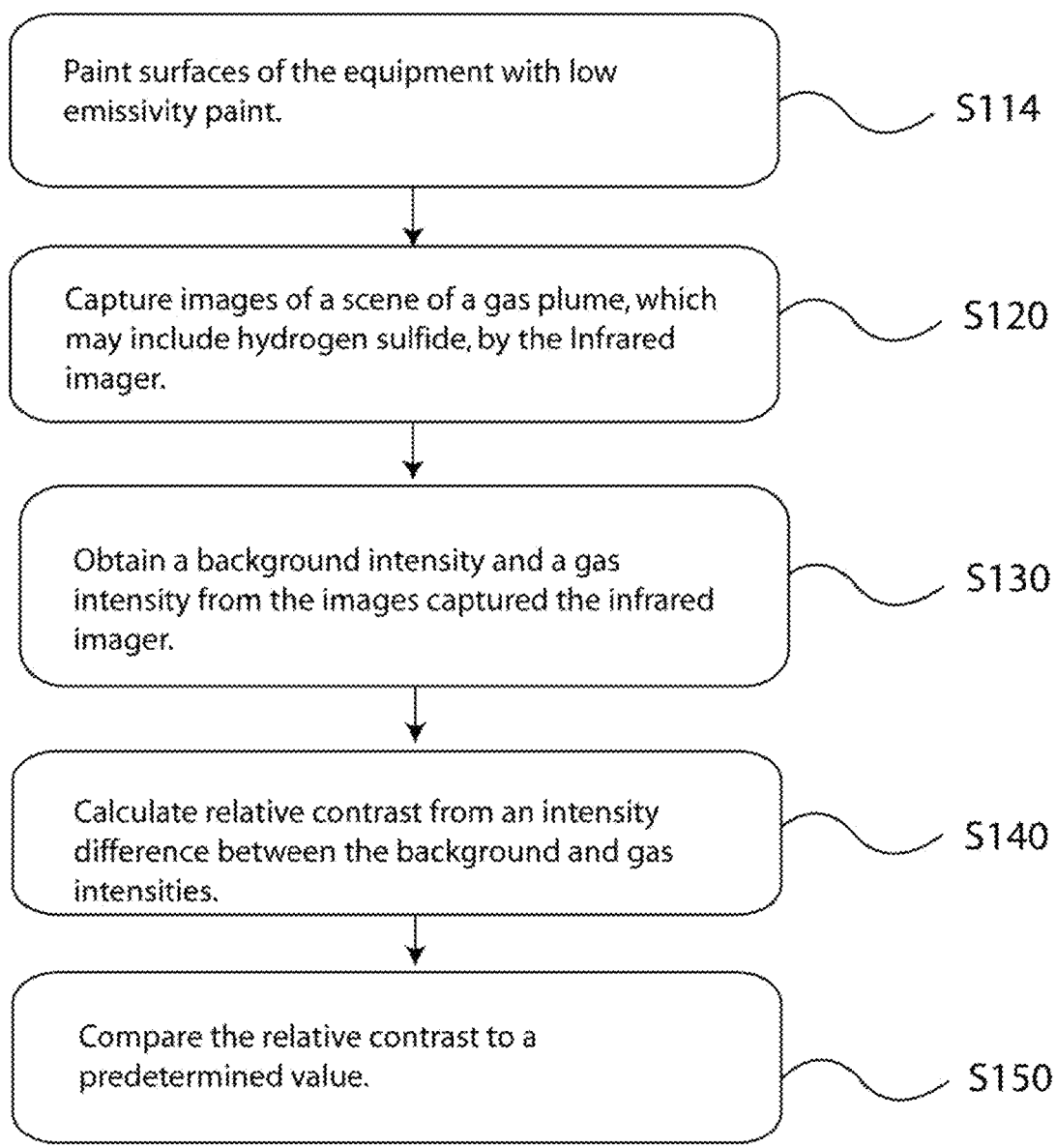
FIG. 18 shows a flowchart for the method for detecting hydrogen sulfide ($H_2S$) in gas plume constructed as still another embodiment of the present invention.

Another embodiment for a method for detecting hydrogen sulfide ($H_2S$) in gas plume is illustrated in the flowchart shown in FIG. 17. The processes in this embodiment, shown in FIG. 17, include one more step S112 than the processes shown in FIG. 16, and other processes are substantially the same as the processes shown in the flowchart of FIG. 16. Therefore, descriptions for the same processes will be skipped. Referring FIG. 17, an illuminator 150 is turned on to illuminate the scene of a gas plume that may include hydrogen sulfide (S112). The illuminator works as an active source to illuminate the scene with infrared light in the spectral window of the bandpass filter 120 installed in the IR imager 110.

Experiment setup for imaging hydrogen sulfide ($H_2S$).

Figure 19:
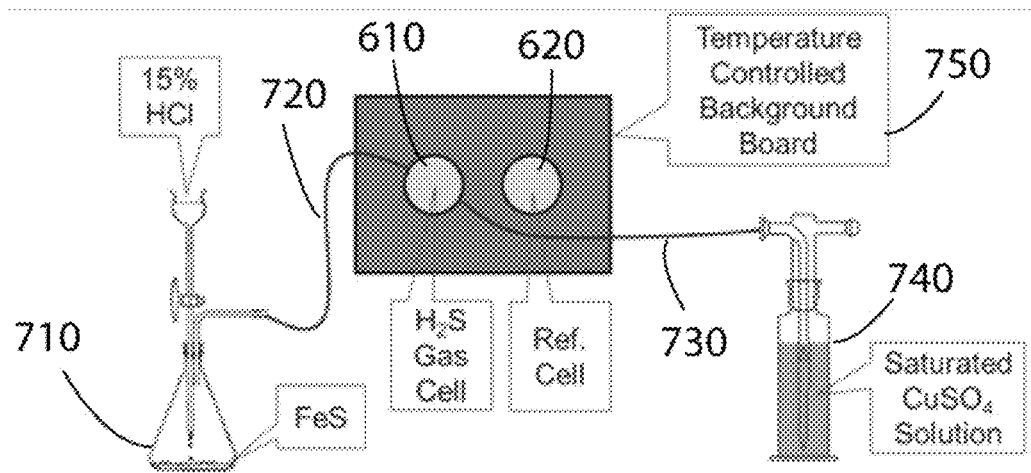
FIG. 19 shows an experiment setup for generating and removing hydrogen sulfide gas.

This invention has been verified and demonstrated by an experiment. Hydrogen sulfide ($H_2S$) gas is highly toxic. To minimize the risk associated with handling hydrogen sulfide, the hydrogen sulfide gas is generated in a completely closed system as illustrated in FIG. 19. The closed system is placed in a well ventilated location as a contingency safety measure. Very strict safety procedures is followed in every step involving hydrogen sulfide.

As illustrated in FIG. 19, hydrogen sulfide gas is generated by gently adding 15% hydrogen chloride (HCl) solution to ferrous sulfide (FeS) powder in the container 710. The concentration of HCl is not limited to 15% as long as it has sufficient strength to react with FeS and produce $H_2S$ gas. The hydrogen sulfide gas travels through tubing 720 and fills the gas cell 610. The reference cell 620 is constructed in the same way as gas cell 610, and pure air flows through the reference cell 620. Both gas cell 610 and reference cell 620 have windows that have high transmittance in the infrared region of the interest so that the imager can see through the cells to the temperature controlled background board 750. Both gas cell 610 and reference cell 620 are in the field of view of the imaging system discussed above. Hydrogen sulfide gas is pushed through the gas cell 610 and another tubing 730 into an absorber 740 (a gas scrubbing bottle) that contains saturated copper sulfate ($CuSO_4$) solution. The amount of $CuSO_4$ solution is at least two times of the amount required to neutralize the amount of hydrogen sulfide generated.

Before hydrogen sulfide gas is generated, the two cells in FIG. 19, the gas cell 610 and the reference cell 620, have virtually the same intensities (same darkness in an IR image). The reference cell 620 works as a background as described above. As hydrogen sulfide gas is generated, and the hydrogen sulfide cell 610 is filled with hydrogen sulfide, the image of hydrogen sulfide cell 610 will become darker (assuming the background board is warmer, otherwise it will be lighter). This will demonstrate the feasibility of imaging hydrogen sulfide. An experiment using the setup as illustrated in FIG. 19 and an IR imager has shown the contrast consistent with the contrast predicted and presented in the table in FIG. 9.

While this invention has been described in connection with what is presently considered to be practical exemplary embodiments, it is to be understood that the invention is not limited to the disclosed embodiments, but is intended to cover various modifications and equivalent arrangements included within the scope of the claims.

What is claimed is:

1. An imaging system for detecting hydrogen sulfide, comprising:
    an infrared (IR) imager capable of capturing an image of a scene that includes a gas plume, the infrared imager including a sensor to detect the image; and
    a bandpass filter installed in the infrared imager, the image of the scene passing through the bandpass filter, the bandpass filter having a spectral window, light having a wavelength in the spectral window of the bandpass filter passing the bandpass filter while light having a wavelength outside the spectral window is blocked in the bandpass filter, a width of the spectral window being in a range of 100 nm to 300 nm, the spectral window placed in a wavelength range in which a relative contrast $(\Delta I/I_B) > 3.0\%$ when $\Delta T < 100°$ C. and $CL=100,000$ ppm-m where $\Delta I = I_B - I_G$, $I_G$ is an intensity of the gas plume, $I_B$ is an intensity of a background that does not include the gas plume, $\Delta T$ is a difference between a background apparent temperature and a temperature of the gas plume, C is a concentration of the hydrogen sulfide, and L is an optical path length of the gas plume.

2. The imaging system of the claim 1, further comprising an illuminator to illumine the scene with an infrared light.

3. The imaging system of the claim 2, comprised of a wavelength of the infrared light of the illuminator including the wavelength range of the spectral window of the bandpass filter.

4. The imaging system of the claim 1, comprised of the sensor of the infrared imager being a long-wave infrared (LWIR) sensor if the bandpass filter has the spectral window positioned in the wavelength range between 7.0 µm and 10.0 µm.

5. The imaging system of the claim 1, comprised of the sensor of the infrared imager being a short-wave infrared (SWIR) sensor if the bandpass filter has the spectral window positioned in the wavelength range between 2.5 µm and 2.8 µm.

6. The imaging system of the claim 1, comprised of the sensor of the infrared imager being a short-wave infrared (SWIR) sensor if the bandpass filter has the spectral window positioned in the wavelength range between 1.5 µm and 2.0 µm.

7. The imaging system of the claim 1, comprised of the spectral window of the bandpass filter included in a wavelength range between 2.55 µm and 2.7 µm.

8. The imaging system of the claim 1, comprised of the spectral window of the bandpass filter included in a wavelength range between 8.0 µm and 8.1 µm.

9. The imaging system of the claim 1, comprised of the spectral window of the bandpass filter included in a wavelength range between 1.9 µm and 2.0 µm.

10. The imaging system of the claim 1, further comprising:
    an analysis unit coupled to the infrared imager for analyzing the image of the scene, the analysis unit including a machine readable storage medium that provides instructions that cause a machine apparatus to perform operations to determine whether the gas plume includes the hydrogen sulfide, the operations comprising:
    obtaining an intensity of a background, which does not include the gas plume, from the image of the scene;
    obtaining an intensity of the gas plume from the image of the scene;
    calculating intensity difference between the intensities of the background and the gas plume;
    calculating a relative contrast that is the intensity difference divided by the intensity of the background; and
    determining whether the relative contrast is higher than a predetermined value.

11. A method for detecting hydrogen sulfide contained in a gas plume, the method comprising:
    capturing an image of a scene that includes the gas plume by an infrared imager, the infrared imager including a sensor to detect the image, a bandpass filter installed in the infrared imager, the image of the scene passing through the bandpass filter, the bandpass filter having a spectral window, light having a wavelength in the spectral window of the bandpass filter passing the bandpass filter while light having a wavelength outside the spectral window is blocked in the bandpass filter, a width of the spectral window being in a range of 100 nm to 300 nm, the spectral window positioned in a wavelength range in which a relative contrast $(\Delta I/I_B) > 3.0\%$ when $\Delta T < 100°$ C. and $CL=100,000$ ppm-m where $\Delta I = I_B - I_G$, $I_G$ is an intensity of the gas plume, $I_B$ is an intensity of a background that does not include the gas plume, $\Delta T$ is a difference between a background apparent temperature and a temperature of the gas plume, C is a concentration of the hydrogen sulfide, and L is an optical path length of the gas plume;
    obtaining an intensity of a background, which does not include the gas plume, from the image of the scene;
    obtaining an intensity of the gas plume from the image of the scene;
    calculating intensity difference between the intensities of the background and the gas plume;
    calculating a relative contrast that is the intensity difference divided by the intensity of the background; and
    determining whether the relative contrast is higher than a predetermined value.

12. The method of the claim 11, further comprising illumining the scene with an infrared light by an illuminator.

13. The method of the claim 12, comprised of a wavelength of the infrared light of the illuminator including the wavelength range of the spectral window of the bandpass filter.

14. The method of the claim 11, comprised of the sensor of the infrared imager being a long-wave infrared (LWIR) sensor if the bandpass filter has the spectral window positioned in the wavelength range between 7.0 µm and 10.0 µm.

15. The method of the claim 11, comprised of the sensor of the infrared imager being a short-wave infrared (SWIR) sensor if the bandpass filter has the spectral window positioned in the wavelength range between 2.5 µm and 2.8 µm.

16. The method of the claim 11, comprised of the sensor of the infrared imager being a short-wave infrared (SWIR) sensor if the bandpass filter has the spectral window positioned in the wavelength range between 1.5 µm and 2.0 µm.

17. The method of the claim 11, comprised of the spectral window of the bandpass filter included in a wavelength range between 2.55 μm and 2.7 μm.

18. The method of the claim 11, comprised of the spectral window of the bandpass filter included in a wavelength range between 8.0 μm and 8.1 μm.

19. The method of the claim 11, comprised of the spectral window of the bandpass filter included in a wavelength range between 1.9 μm and 2.0 μm.

* * * * *